United States Patent [19]

Landscheidt

[11] Patent Number: 4,555,581

[45] Date of Patent: Nov. 26, 1985

[54] PROCESS FOR THE PRODUCTION OF 7-OXABICYCLO (2.2.1)HEPT-5-ENE DERIVATIVES

[75] Inventor: Alfons Landscheidt, Krefeld, Fed. Rep. of Germany

[73] Assignee: Chemische Fabrik Stockhausen GmbH, Krefeld, Fed. Rep. of Germany

[21] Appl. No.: 534,533

[22] Filed: Sep. 22, 1983

[30] Foreign Application Priority Data

Sep. 24, 1982 [DE] Fed. Rep. of Germany ....... 3235399

[51] Int. Cl.$^4$ ........................................... C07D 307/00
[52] U.S. Cl. .................................................. 549/463
[58] Field of Search ........................................ 549/463

[56] References Cited

PUBLICATIONS

Brion, Tetrahedron Letters, 23(50), pp. 5299–5302, (Dec. 1982).
Dunlop et al., The Furans, pp. 54–59, 63–67, (1953).
Kunstmann et al., J. Am. Chem. Soc., vol. 82, pp. 4115–4119, (1962).
Oullette et al., J. Org. Chem., pp. 4302–4303, (1968), vol. 33(11).
Dauben et al., J. Am. Chem. Soc., vol. 98(7), pp. 1992–1993, (1976).
Moore et al., J. Org. Chem., vol. 48, pp. 1105–1106 (1983).
Nelson et al., J. Heterocyclic Chem., vol. 9(3), pp. 561 and 565, (1972).

*Primary Examiner*—Henry R. Jiles
*Assistant Examiner*—Bernard I. Dentz
*Attorney, Agent, or Firm*—Sprung Horn Kramer & Woods

[57] ABSTRACT

The invention relates to a process for the production of 7-oxabicyclo-(2,2,1)hept-5-ene derivatives by conversion of acrylic acid esters and furanes in the presence of catalytic quantities of a Lewis acid. By use of Lewis acid, the reaction time is greatly reduced with good results in terms of product purity by comparison with known processes. The reaction products are intermediates, e.g. in the production of N-substituted acrylic acid amides.

10 Claims, No Drawings

PROCESS FOR THE PRODUCTION OF 7-OXABICYCLO (2.2.1)HEPT-5-ENE DERIVATIVES

The present invention relates to a process for the production of 7-oxabicyclo(2,2,1)hept-5-ene derivatives.

The conversion of esters of $\alpha,\beta$-unsaturated acids with furans to 7-oxabicyclo(2.2.1)hept-5-ene derivatives according to the Diels-Alder reaction is known:

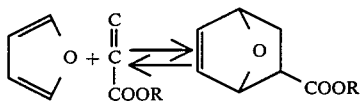

REACTION

Like all Diels-Alder reactions, the reaction leads to a change of equilibrium that is dependent on the reaction components that are used and on the reaction parameters of temperature and pressure.

Up to now, the protracted reaction time, that has been attributable to a very low reaction speed, has been a disadvantage. The furan/ethyl acrylate reaction took several weeks until the conversion amounted to 21% (M. P. Kunstmann et al, Journ. Am. Chem. Soc. 82 (1962), 4119). The conversion of furan with methylacrylate leads to a conversion of only 18% under analogous conditions (R. J. Quellette et al, Journ. Org. Chem. Soc. 33 (1968), 4303). A reduction of the reaction time to a few hours can be achieved by a technically expensive increase in pressure to 15 kbar (W. G. Dauben, H. O. Krabbenhoft, Journ. Am. Chem. Soc. 98 (1976), 1992). The reaction time can be reduced to several days if a more reactive dienophile such as acryloyl chloride is used in place of the ester. The Diels-Alder adduct of the furan results in a high yield when this is done. If, on the other hand, 2-methylfurane is used as the diene, the corresponding product of the addition-substitution reaction is formed as follows (T. A. Eggelte et al, Heterocycles 4 (1967), 19-22):

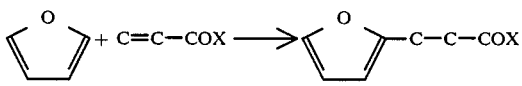

It is thus an object of the present invention to provide a process for the production of Diels-Alder adducts of furans and acrylic acid esters in high yields and requiring only short reaction times.

Most surprisingly, it has now been found that the conversion of acrylic acid esters with furans to form 7-oxabicyclo(2.2.1)hept-5-ene derivatives can be effected in a few minutes if the reaction is performed in the presence of catalytic quantities of Lewis acids. This is particularly surprising since Lewis acids favour the addition-substitution reaction, as is well known (A. P. Dunlop, F. N. Peters, "The Furanes" Reinhold Publishing Co., New York, 1953).

According to this invention, furans (if necessary, substituted furanes) and acrylic acid esters of alcohols with 1 to 22 C-atoms are converted in the presence of catalytic quantities of a Lewis acid, to the 7-oxabicyclo(2.2.1)hept-5-ene derivatives.

The conversion can be completed at room temperature or below. Low temperatures shift the equilibrium to the product side. The conversion is normally carried out in a temperature range of 0°-40° C., preferably between 15° and 25° C.

All the familiar Lewis acids such as $AlCl_3$, $TiCl_4$, $SnCl_4$, $FeCl_3$ and $BF_3.OET_2$ can be used as catalysts. It is especially preferred that $AlCl_3$ be used. Acrylic acid methylester is preferred as the ester component, and furane is preferred as the furan component. In order to carry out the conversion, the Lewis acid is preferably dissolved in the $\alpha,\beta$-unsaturated ester and the furan added drop-wise during cooling. The Diels-Alder adduct forms spontaneously. When the exothermic reaction has subsided, the organic phase is separated after decomposition of the Lewis acid with water and at first non-reacted furan and $\alpha,\beta$-unsaturated ester is distilled off. The crude product so obtained can only be distilled in large batches under carefully-controlled conditions, preferably continuously—e.g., in a thin-film evaporator—and preferably in a vacuum, for otherwise decomposition into the starting components (the reverse Diels-Alder reaction) will occur.

The reaction products are valuable intermediate products for many synthesis, e.g., the production of extremely pure N-substituted acrylic acid amide, by conversion with primary or secondary amines and thermal splitting of the product.

The invention will now be described further by way of example only and with reference to the following:

EXAMPLE 1

4.5 g (0,033 Mol) $AlCl_3$ are added to 100 g (1 Mol) ethylacrylate and dissolved with stirring. 68 g (1 Mol) furane is then added drop-wise, during cooling to 20° to 25° C. After one hour, the exothermic reaction is terminated, followed by stirring for one hour at 25° C. and 30 g water is added. The organic phase is separated. First, the non-converted furane and ethylacrylate is distilled off under a pressure of 10 Torr. The 2-carbomethoxy-7-oxabicyclo(2.2.1)hept-5-ene boils at 60° C. and is obtained in a yield of 67.2 g (40% theoretical).

IR, NMR and CH analyses confirm the structure.

EXAMPLE 2

43 g (0.5 Mol) methylacrylate is prepared and 2.3 g (0.016 Mol) $AlCl_3$ added thereto and dissolved with stirring. At 20°-25° C., 48 g (0.5 Mol) 2,5-dimethylfurane is drop-wise and the temperature is maintained at 20° C. until the weak exothermic reaction is finished, and stirring is continued for a further hour. 20 g of water is added, the organic phase separated off and the uncovered 2,5-dimethylfurane and the methalacrylate distilled off under a pressure of 10 Torr. The residue is distilled under a pressure of 0.1 Torr. The 2-carbomethoxy-1,4-dimethyl-7-oxabicyclo(2.2.1)hept-5-ene boils at 40° C. and is obtained in a yield of 27.3 g (30% theoretical).

IR, NMR and CH analyses confirm the structure.

EXAMPLE 3

1290 g (15 Mol) methylacrylate is prepared and 67.5 g (0.5 Mol) $AlCl_3$ added thereto and dissolved with stirring. At 20° to 25° C., 1050 g (15.4 Mol) furane is added drop-wise during cooling. The temperature is maintained at 20° C. until the exothermic reaction is finished, after which stirring is continued for a further hour at 20° C. and then for 3 hours at 10° C. 300 g water is then added, the organic phase separated, and the unconverted furane and the methylacrylate distilled off under a pressure of 10 Torr and at a bath temperature of 60° C. in a rotary evaporator. Finally, the vacuum is lowered to 1 Torr and further volatile components drawn off. The crude product is passed to a thin-film evaporator under a vacuum of 1 Torr and a thermostatically controlled temperature of 95° C. A distillation temperature of approximately 70° C. is used. The 2-carbomethoxy-7-oxabicyclo(2,2,1)hept-5-ene is obtained in a yield of 1060 g (45.9% theoretical).

IR, NMR and CH analyses confirm the structure.

EXAMPLE 4

3.3 g (0.013 Mol) $SnCl_4$ is added to 64 g (0.5 Mol) butyl acrylate and dissolved with stirring. Then during cooling to 20° to 25° C., 34 g (0.5 Mol) furane is added drop-wise. The exothermic reaction finishes after one hour, after which stirring is continued for one hour at 25° C. and 30 g of water added. The organic phase is separated. First, the unconverted furane is distilled off under a pressure of 10 Torr, and then the residue is distilled under a pressure of 0.02 Torr. The 2-carbobutoxy-7-oxabicyclo(2.2.1)hept-5-ene boils at 65° C. and is obtained in a yield of 34.3 g (35% of the theoretical).

IR, NMR and CH analyses confirm the structure.

EXAMPLE 5

2.5 g (0.013 Mol) $TiCl_4$ is added to 120 g (0.5 Mol) dodecylacrylate and dissolved with stirring. Then during cooling to 20°–25° C., 34 g (0.5 Mol) furane is added drop-wise. The exothermic reaction ends after one hour, and stirring is continued for one hour at 25° C. and 30 g water added. The organic phase is separated and the unconverted furane and dodecylacrylate are distilled at under a pressure of 1 Torr. The 2-carbodecyloxy-7-oxabicyclo(2.2.1)hept-5-ene is obtained in a yield of 69.3 g (45% theoretical).

IR, NMR and CH analyses confirm the structure.

The embodiments of the invention in which an exclusive property or privilege is claimed are defined as follows:

1. A process for the production of a 7-oxabicyclo(2.2.1)hept-5-ene 2-carboxylic acid alkyl ester compound, comprising reacting a furan and an ester of acrylic acid with an alcohol of 1 to 22 C-atoms in the presence of a catalytic quantity of a Lewis acid.

2. A process according to claim 1, wherein said furan is a substituted furan.

3. A process according to claim 1, wherein the reaction is carried out at a temperature between 0° and 40° C.

4. A process according to claim 3, wherein said temperature is between 15° and 25° C.

5. A process according to claim 1, wherein the Lewis acid is selected from the group consisting of $AlCl_3$, $TiCl_4$, $SnCl_4$, $FeCl_3$ and $BF_3.OET_2$.

6. A process according to claim 1, wherein the ester is acrylic acid methyl ester.

7. A process according to claim 1, wherein said furan is furan.

8. A process according to claim 1, wherein the Lewis acid is decomposed, any unconverted furan compound and ester of acrylic acid are separated out and the crude product obtained thereby is distilled under controlled conditions.

9. A process according to claim 8, wherein said crude product is distilled under vacuum.

10. A process according to claim 1, wherein the Lewis acid is $AlCl_3$.

* * * * *